United States Patent [19]

Thomas, Jr.

[11] Patent Number: 5,127,913
[45] Date of Patent: Jul. 7, 1992

[54] APPARATUS AND METHOD FOR IMPLANTING AN INTRAMEDULLARY ROD

[76] Inventor: Charles B. Thomas, Jr., 17 Woodvale Ave., Greenville, S.C. 29605

[21] Appl. No.: 688,473

[22] Filed: Apr. 22, 1991

[51] Int. Cl.⁵ .............................................. A61F 5/04
[52] U.S. Cl. ........................................ 606/62; 606/95
[58] Field of Search ................................ 606/62-64, 606/95-98; 128/899

[56]  References Cited

U.S. PATENT DOCUMENTS

| | | | |
|---|---|---|---|
| 4,621,628 | 11/1986 | Brudermann | 606/64 X |
| 4,846,162 | 7/1989 | Moehring | 606/64 X |
| 4,877,019 | 10/1989 | Vives | 606/64 |
| 4,913,137 | 4/1990 | Azer et al. | 606/96 X |

*Primary Examiner*—Robert A. Hafer
*Assistant Examiner*—Brian E. Hanlon
*Attorney, Agent, or Firm*—Cort Flint

[57] ABSTRACT

Apparatus and method for locating distal locking holes in an implanted intramedullary rod is disclosed. An insert member having at least one high-energy permanent magnet carried with its poles along an axis transverse to a longitudinal axis of the insert member at a distal end thereof is disclosed. The insert member is inserted into an implanted intramedullary rod and aligned so that the poles of the high-energy permanent magnet(s) are aligned with an axis of the distal locking hole(s) of the implanted intramedullary rod. A detector magnet, also constructed from a high-energy magnetic material, is utilized to find the location of the distal locking hole axis by means of attraction to the inserted high-energy magnet. It has been found that by using a high-energy magnetic material such as neodymium, a high force of attraction can exist exterior of the bone to locate the axis. An indication of this location may be made with a marking instrument and a hole drilled through the bone and distal locking hole for insertion of a distal locking screw.

23 Claims, 2 Drawing Sheets

APPARATUS AND METHOD FOR IMPLANTING AN INTRAMEDULLARY ROD

BACKGROUND OF THE INVENTION

The invention relates to an apparatus and method for implanting an intramedullary rod for fixation of a fracture in a long bone such as the femur, and particularly, to an apparatus and method for detecting the location of the distal screw holes in such an intramedullary rod for locking the rod in place.

A severe fracture in a long bone such as a femur or tibia, tends to cause the fractured bone segments to compress, shortening the length of the bone. A traditional treatment is to use an intramedullary rod inserted into an opening made in one end of the bone and affixed to the bone segments. The intramedullary rod substantially occupies the medullary canal, and must be affixed or locked to the bone segments on each side of the fracture to prevent shortening or rotation of the bone. One problem in the locked intramedullary rod technique is locating the distal hole(s) in the distal end of the rod and successfully aligning transverse screws with the hole(s) for insertion through the bone wall. One known technique for locating a distal hole is an X-ray imaging technique that utilizes a free hand technique. The image intensifier (fluoroscope) is interactively repositioned until an accurate circular image of the rod hole is produced. This occurs when the image intensifier is located on the center line of the hole. The insertion point for the transverse screws may then be determined. The problem with this technique is the exposure of the patient and the operating team to X-radiation which can be excessive if the procedure to properly locate the distal holes results in a large number of attempts. In particular, the hands may be excessively exposed to the X-radiation. Even if protective gloves and clothing are utilized, the effects of excessive exposure to X-radiation are not entirely eliminated. In addition, if correct alignment is not obtained, multiple perforations of the bone may occur.

Other techniques have been proposed for locating the distal holes in an implanted intramedullary rod which do not require X-ray imaging techniques. For example, U.S. Pat. No. 4,881,535 discloses a mechanical jig that is accurately retained in relationship to the rod by a portion extending into the bone through the opening made in the proximal end of the bone. The jig includes an external portion that extends parallel to the bone for aligning screws with the apertures in the rod provided along the externally extended portion of the jig. This technique may be successful, however, there is an opportunity for relative movement between the jig and the rod which may result in misalignment. U.S. Pat. No. 4,877,019 discloses an electrical probe which may be inserted into a hollow interior of an intramedullary rod for generating an electrical field which may be detected through the distal intramedullary holes. An oscilloscope signal may be utilized to visibly display the alignment of the distal holes. U.S. Pat. No. 4,621,628 discloses a similar technique wherein an electrical probe inserted in the hollow interior of an intramedullary rod detects an axially symmetrical field generated by at least one magnet on the outside of the bone. The successful use of devices using electronic imaging depends upon qualified operators of the electronic equipment and proper functioning of the equipment. The imaging techniques are relatively complex and require additional electronic equipment and visual displays in the operation area. The costs of the techniques in terms of the task accomplished also is a consideration which may weigh against their success and use.

Accordingly, an object of this invention is to provide a simple yet reliable apparatus and method for locating the distal holes in an implanted intramedullary rod so that screws can be inserted through the bone and rod to transfix the rod at the distal femur.

Another object of the invention is to provide an apparatus and method for implanting and transfixing an intramedullary rod within the intramedullary canal of a long bone which is simple and does not require the use of electronic equipment.

Another object of the invention is to provide an apparatus and method for implanting an intramedullary rod and locating the distal holes in the rod using high-energy magnets for accurate alignment of the distal holes and screws for insertion through the bone.

SUMMARY OF THE INVENTION

The above objectives are accomplished according to the present invention by providing an apparatus and method for locating the distal holes in an intramedullary rod implanted in a long bone by providing an elongated insert member which is inserted in a hollow interior of the intramedullary rod. A plurality of high-energy magnets are carried by the insert member having magnetic poles oriented along an axis transverse to a longitudinal axis of the insert member and concentric with an axis of the distal locking holes of the intramedullary rod. An indicator aligns the insert member and the magnets at an aligned position so that the axes of the magnets and distal locking holes are aligned. A detector magnet for detecting a magnetic field generated by the aligned high-energy magnets through the distal locking holes is disposed at a location exterior of the bone. The insert magnets and detector magnet are constructed from a high-energy magnetic material which includes neodymium. A detector may also comprise a transparent element containing metallic particles, and an indicator is formed on the transparent element so that the metallic particles center around the indicator when aligned with the magnetic axis of the magnets.

In accordance with the method of the invention, an intramedullary rod is implanted and affixed within an intramedullary canal of a long bone. The intramedullary rod is affixed to the proximal end of the bone by a proximal locking screw inserted through the proximal locking hole after the distal screws have been placed. To place the distal screws, an elongated insert member is introduced through an opening in the intramedullary rod into a hollow interior of the intramedullary rod. An elongated insert member is selected having at least one permanent magnet carried at the distal end of the insert member composed of a high-energy magnetic material. The method then includes aligning the permanent magnet with at least one distal locking hole of the intramedullary rod so that a high-energy magnetic field is generated along an axis aligned with the distal locking holes; and detecting the magnetic field along the axis exterior of the bone by using a detector which detects the magnetic field. An incision is formed at a distal portion of the leg in the vicinity of the distal locking hole. The magnetic field is detected and the location of the axis of the distal locking hole is indicated. A hole is drilled through the bone extending through the distal locking hole of the intramedullary rod. At least one distal locking screw is inserted through the bone and distal locking hole of the intramedullary rod. Preferably, an elongated insert member is selected having a pair of the permanent magnets disposed transverse to a longitudinal axis of the insert member at spaced positions corresponding to positions of a pair of distal locking holes, and at a position in which the permanent magnets have magnetic axes aligned with their magnetic poles and the axis of a pair of the distal locking holes. The permanent magnets are constructed from a high-energy magnetic material which includes neodymium. The method contemplates detecting the magnetic field and distal locking hole axes by using a transparent detector having an indicator with metallic particles surrounding the indicator so that the magnetic particles are centered around the indicator with the axis of the magnetic field, or a detector magnet composed of high-energy magnetic material having magnetic poles lying along a magnetic axis. The magnetic axis of the detector magnet is disposed relative to one of the inserted permanent magnets so that the detector magnet is attracted to the permanent axis at a location corresponding to the distal locking hole exterior of the bone.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figures 1, 2, 3:
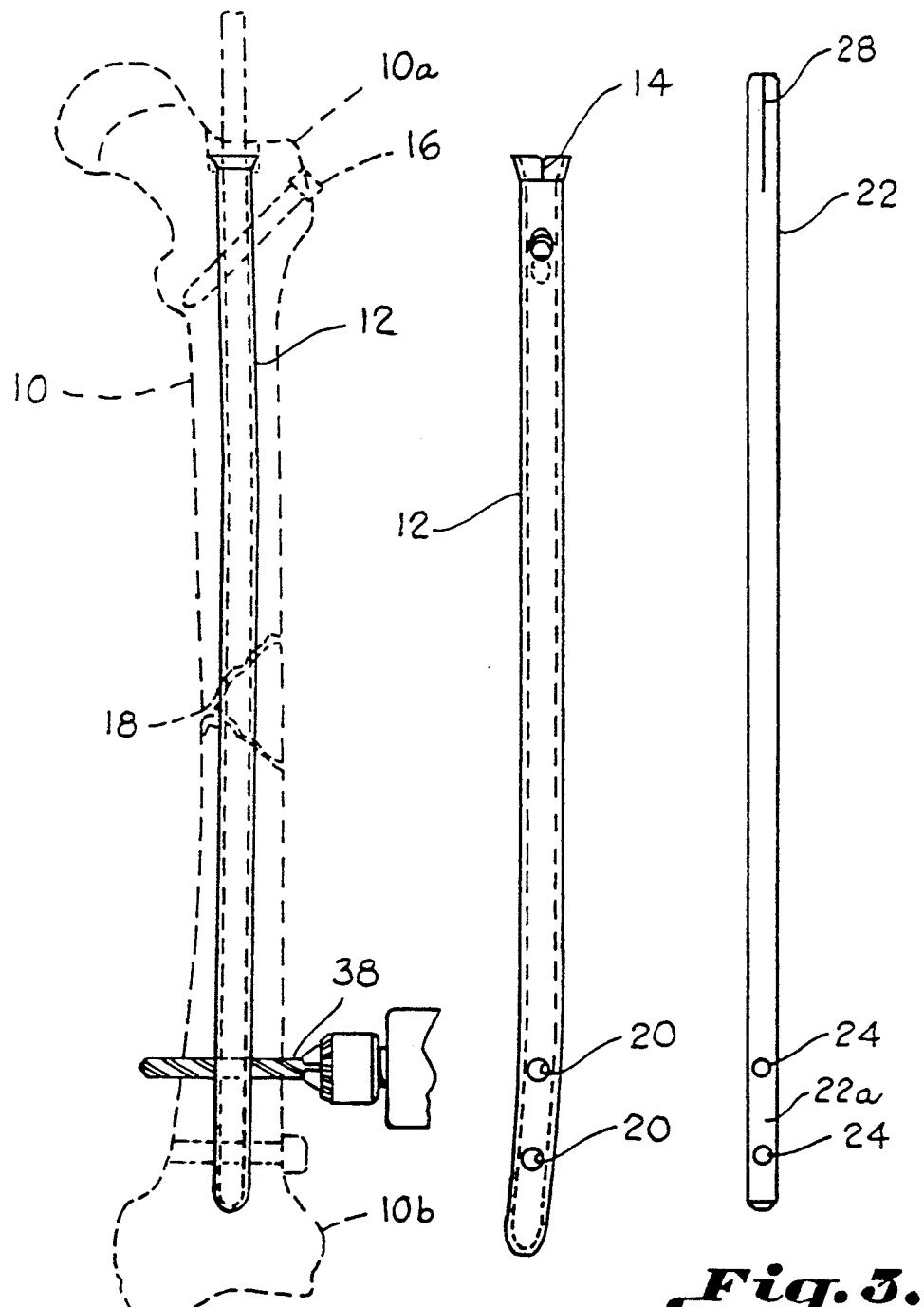
FIG. 1 is a front elevation illustrating an intramedullary rod implanted into a long bone in accordance with the apparatus and method of the present invention.
FIG. 2 is a side elevation of an intramedullary rod for implantation according to the invention.
FIG. 3 is a side elevation of an insert member having a pair of spaced permanent magnets in alignment with distal locking holes of the intramedullary rod of FIG. 2.

Referring now in more detail to the drawings, a long bone 10 such as a femur is illustrated in which an intramedullary rod 12 is implanted. Intramedullary rod 12 may be a conventional intramedullary rod, but includes an indicator or score line 14 for purposes which will be described later. Typically, intramedullary rod 12 is constructed from a 316 stainless steel material which is supposedly non-magnetic. However, it has been found that this stainless steel allows some magnetic flux to be generated through the material. The procedure for implanting intramedullary rod 12 within the medullary canal of a femur is conventional, and has not been illustrated. As can be seen in FIG. 1, intramedullary rod 12 is implanted in a long bone such as femur 10. The problem of locking the distal femur 10b and intramedullary rod 12 together in accordance with the present invention will now be described which prevents shortening or mal-rotation of the fractured bone segments 18.

Figure 4:
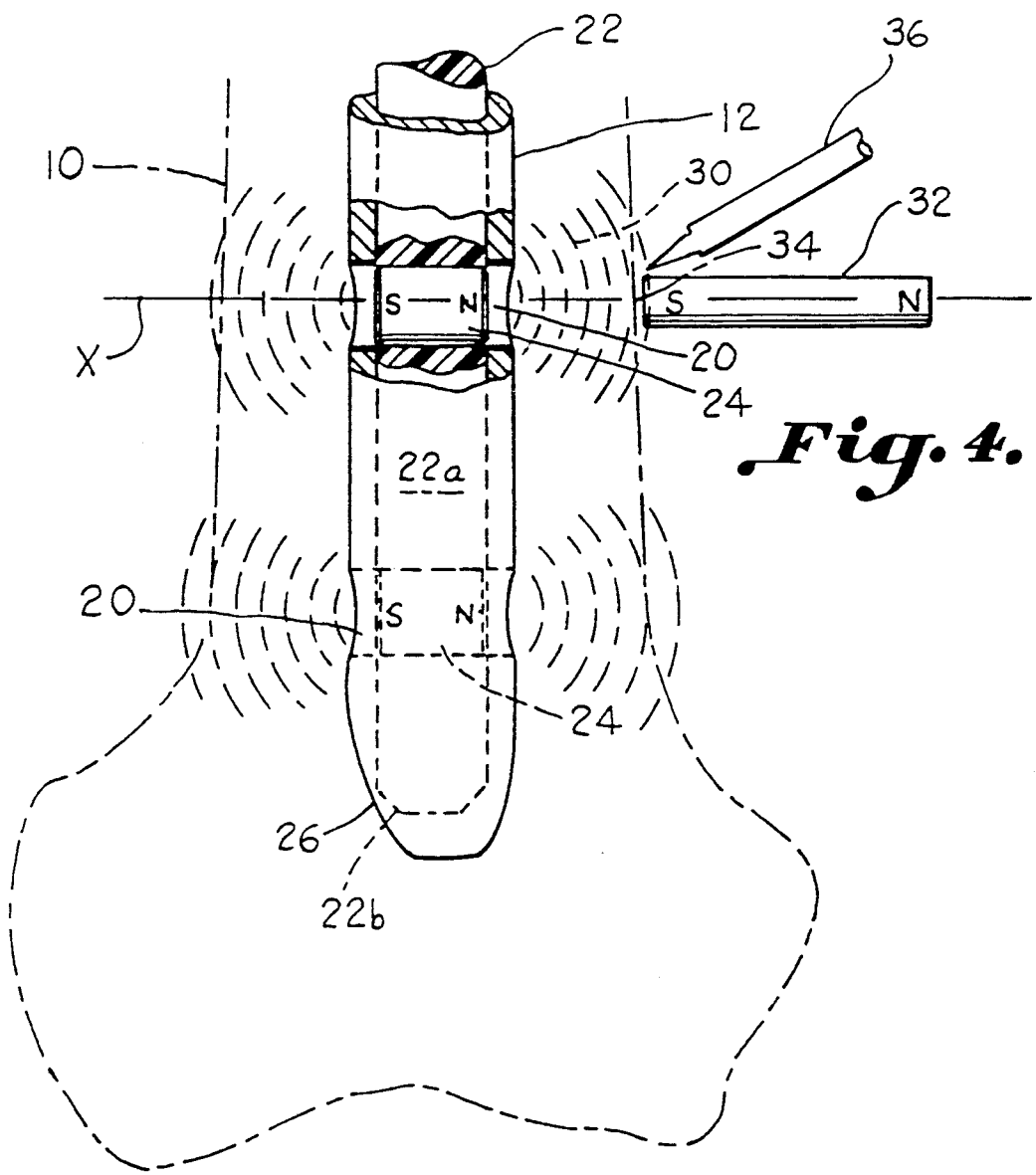
FIG. 4 is an enlarged front elevation illustrating a distal portion of a long bone such, as a distal femur and apparatus and method for locating distal holes in implanted intramedullary rod according to the invention.
Figure 5:
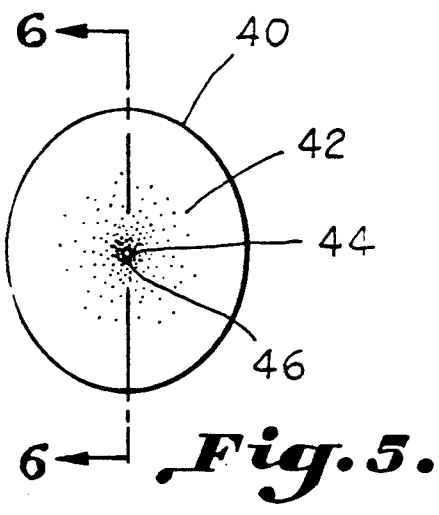
FIG. 5 is an alternate embodiment of a detector for detecting a magnetic field of permanent high-energy magnets aligned with the distal locking holes of an intramedullary rod.
Figure 6:
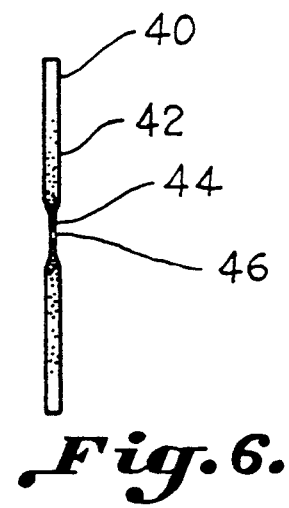
FIG. 6 is a sectional view taken along line 6—6 of FIG. 5.

Intramedullary rod 12 may include one or more distal locking holes 20. While the invention will be described with an intramedullary rod having a pair of holes 20, it is to be understood, of course, that the invention may be utilized with an intramedullary rod having only a single distal locking hole and screw. There is an elongated insert member 22 which is constructed from a sterilizable and non-magnetic material, such as plastic. At a distal end 22a, insert member 22 includes a pair of spaced high-energy magnets 24 which are affixed within insert member 22 at longitudinally spaced locations corresponding to distal locking holes 20. For this purpose, insert member 22 may include a terminal end 22b designed to bottom out and engage a corresponding portion of a terminal end of intramedullary rod 12 at 26, as can best be seen in FIG. 4. Indicators for aligning the poles of magnets 24 with an axis X corresponding to the longitudinal axis of distal locking holes 20 is provided by a score 28 on insert member 22. Score 28 of insert member 22 and score 14 of intramedullary rod 12 may be aligned so that a longitudinal axis of cylindrical bar magnets extending through the holes of the magnets coincides with axis X of distal locking holes 20. Means for detecting a magnetic field 30 generated by magnets 24 includes a high-energy detector magnet 32 which may also be constructed from a high-energy magnetic material. It has been found, according to the invention, that distal locking hole magnets 24 and detector magnet 32 may be constructed from a high-energy material which includes neodymium. High-energy magnets constructed from that high-energy material have been found to be of sufficient strength through bone material of bone 10 that detector magnet 32 is strongly attracted to a location 34 exterior of bone 10 which lies on axis X of distal locking holes 20, as can best be seen in FIG. 4. Suitable magnets are available from Bunting Advanced Magnetic Materials of Newton, Kans., designated as Neodymium "27" permanent magnets. It has been found that bar magnets having a diameter corresponding to the diameter of distal locking holes 20 and corresponding in length to the inner diameter of intramedullary rod 12 have sufficient energy to attract each other from a distance of ten inches apart. At the exterior of bone 10, only an inch or so apart, the attraction of the magnets is high, causing the magnets to lock in attraction along axis X of distal locking hole 20 and along poles of the magnet when properly aligned as described above in reference to scores 14, 28, and axial position of insert 22 as determined by placement of distal end 22a at the distal end 26 of intramedullary rod 12. Means for indicating and marking this location at the exterior of bone 10 may be provided by any suitable means such as a marking instrument 36. Alternately, the surgeon may be able to withdraw detector magnet 32 and insert a drill bit 38 keeping his eye on the location of attraction in an accurate manner, thus avoiding the need for marking that location. Another embodiment of a detector means for detecting the distal locking holes with magnets 24 inserted is illustrated in FIGS. 5 and 6 as including a transparent element 40 containing metallic particles 42. Element 40 is dimpled together at 44 so that metal particles 42 form a clear circular pattern around dimple 44 when dimple 44 is aligned with the axis of the poles of magnet 24. Element 40 may include an aperture 46 in dimple 44 whereby a marking instrument, such as 36 may be utilized to mark the location of the distal locking hole axis as detected magnetically or alternatively, a thin wire may be drilled in to the bone through the perforation of the center of the transparent element.

While a preferred embodiment of the invention has been described using specific terms, such description is for illustrative purposes only, and it is to be understood that changes and variations may be made without departing from the spirit or scope of the following claims.

What is claimed is:

1. Apparatus for locating the distal holes in an intramedullary rod implanted in an intramedullary canal of a long bond for affixing said rod to a distal portion of said bone by inserting distal locking screws through said bone and said intramedullary rod comprising:

an elongated insert member for insertion into a hollow interior of said intramedullary rod;

at least one high-energy permanent magnet carried by said insert member transverse to a longitudinal axis of said insert member for alignment with at least one distal locking hole of said intramedullary rod;

means for inserting said insert member and said magnet into said intramedullary rod at an aligned position so that said magnet is aligned with said distal locking holes of said intramedullary rod; and detector means for detecting a permanent magnetic field generated by said high-energy magnet which passes through said distal locking hole at an exterior position of said bone, and said detector means visually indicating said exterior position directly adjacent said bone for forming a bore through said bone in alignment with said distal locking holes for the placement of said distal locking screw.

2. The apparatus of claim 1 wherein said permanent magnet is constructed from a high-energy magnetic material which includes neodymium.

3. The apparatus of claim 1 wherein said detector means comprises a transparent element containing metallic particles, an indicator carried by said transparent element so that said metallic particles center around said indicator when aligned with said permanent magnet.

4. The apparatus of claim 1 wherein said detector means comprises a detector magnet which attracts to said inserted permanent magnet through said bone at a location along an axis of said distal hole.

5. The apparatus of claim 4 wherein said detector magnet is constructed from a magnetic material which includes neodymium.

6. The apparatus of claim 1 wherein said insert member is constructed from a sterilizable, non-magnetic material.

7. The apparatus of claim 1 wherein said means for inserting said insert member and magnet into said intramedullary rod at said aligned position includes a score formed on said insert member by which said insert member is aligned with said intramedullary rod.

8. The apparatus of claim 7 wherein said means for inserting said insert member and said magnet into said intramedullary rod at said aligned position includes a distal end of said insert member corresponding in length to a distal end of said intramedullary rod to position said magnets at a proper position axially of said intramedullary rod corresponding to said axis of said distal locking holes, said score corresponding to a corresponding score on said intramedullary rod so as to align said magnet at a proper rotational position within said intramedullary rod.

9. The apparatus of claim 1 wherein said means for inserting said insert member and magnets into said intramedullary rod at said aligned position includes a score formed on said insert member by which said insert member is aligned with said intramedullary rod.

10. The apparatus of claim 9 wherein said means for inserting said insert member and said magnets into said intramedullary rod at said aligned position includes a distal end of said insert member corresponding in length to a distal end of said intramedullary rod to position said magnets at a proper position axially of said distal intramedullary rod corresponding to said axis of said distal locking holes, said score corresponding to a corresponding score on said intramedullary rod so as to align said magnet at a proper rotational position within said intramedullary rod.

11. Apparatus for locating the distal locking holes in an intramedullary rod implanted in an intramedullary canal of a long bone for affixing said rod to a distal portion of said bone by inserting distal locking screws through said bone and said intramedullary rod, said apparatus comprising:

an elongated insert member for insertion in a hollow interior of said intramedullary rod;

a plurality of high-energy magnets carried by said insert member having magnetic poles oriented along an axis transverse to a longitudinal axis of said insert member and in alignment with an axis of said distal locking holes of said intramedullary rod;

indicator means for aligning said insert member and said magnets at an aligned position so that said magnetic axes are aligned with said axes of said distal locking holes of said intramedullary rod; and detector means for detecting a magnetic field generated by said aligned high-energy magnets emitted through said distal locking holes at an exterior position of said bone, and said detector means visually indicating said exterior position directly adjacent said bone for forming a bore through said bone in alignment with said distal locking holes for the placement of said distal locking screw.

12. The apparatus of claim 11 wherein said magnets are constructed from a high-energy magnetic material which includes neodymium.

13. The apparatus of claim 11 wherein said detector means comprises a transparent element containing metallic particles, an indicator formed on said transparent element so that said metallic particles center around said indicator when aligned with said magnetic axis of said magnets.

14. The apparatus of claim 11 wherein said detector means comprises a high-energy detector magnet which attracts to said high-energy magnets along said axis of said distal locking holes at said exterior bone location.

15. The apparatus of claim 14 wherein said detector magnet is constructed from a high-energy magnetic material which includes neodymium.

16. The apparatus of claim 11 wherein said insert member is constructed from a sterilizable, non-magnetic material.

17. A method for implanting and affixing an intramedullary rod within an intramedullary canal of a long bone comprising the steps of:

implanting an elongated intramedullary rod having proximal and distal locking holes within said medullary canal of said bone;

affixing said intramedullary rod to a proximal head of said bone by means of a proximal locking screw inserted through said proximal locking hole;

introducing an elongated insert member through an opening in said intramedullary rod into a hollow interior of said intramedullary rod;

selecting an elongated insert member having at least one permanent magnet carried at a distal end of said insert member composed of a high-energy magnetic material;

aligning said permanent magnet with at least one distal locking hole of said intramedullary rod so that a high-energy magnetic field is generated along an axis aligned with said distal locking holes;

detecting said magnetic field along said axis at an exterior position of said bone by using a detector means which detects said magnetic field, visually indicating said exterior position directly adjacent said bone with said detector means for forming a bone through said bone in alignment with said distal locking holes for the placement of said distal locking screws.

18. The method of claim 17 including forming an incision at a distal portion of said leg in the vicinity of said distal locking hole, detecting said magnetic field and indicating the location of said axis of said distal locking hole by visually noting the position of said detector means adjacent said bone, and drilling a hole at said position through said bone extending through said distal locking hole of said intramedullary rod.

19. The method of claim 18 including inserting at least one distal locking screw through said bone and distal locking hole of said intramedullary rod; and affixing said intramedullary rod to a proximal head of said bone by means of a proximal locking screw inserted through said proximal locking hole.

20. The method of claim 17 including selecting an elongated insert member having a pair of said permanent magnets disposed transverse to a longitudinal axis of said insert member at spaced positions corresponding to positions of said distal locking holes, and at a position in which said permanent magnets have magnetic axes aligned with their magnetic poles and said axis of a pair of said distal locking holes.

21. The method of claim 20 including selecting said permanent magnets to be constructed from a high-energy magnetic material which includes neodymium.

22. The method of claim 17 including detecting said magnetic field by using a transparent detector having an indicator with metallic particles surrounding said indicator so that said magnetic particles are centered around said indicator when with said axis of said magnetic field.

23. The method of claim 17 including selecting a detector which includes a detector magnet composed of high-energy magnetic material having magnetic poles lying along a magnetic axis, and disposing said magnetic axis of said detector magnet relative to one of said inserted permanent magnets so that said detector magnet is attracted to said permanent axis at a location corresponding to said distal locking hole exterior of said bone.

* * * * *